United States Patent [19]
Costantini et al.

[11] Patent Number: 5,414,155
[45] Date of Patent: May 9, 1995

[54] PREPARATION OF O-DIHYDROXYLATED AROMATIC COMPOUNDS VIA OXIDATION OF O-FUCHSONES

[75] Inventors: Michel Costantini, Lyon; Daniel Manaut, Meyzieu; Daniel Michelet, Saint-Nom-la-Breteche, all of France

[73] Assignee: Rhone-Poulenc Chimie, Courbevoie Cedex, France

[21] Appl. No.: 179,130

[22] Filed: Jan. 10, 1994

[30] Foreign Application Priority Data

Jan. 8, 1993 [FR] France .................. 93 00121

[51] Int. Cl.6 .............................................. C07C 37/60
[52] U.S. Cl. ..................................... 568/771; 568/741; 568/803
[58] Field of Search ............... 568/741, 771, 803, 741, 568/771, 800, 803

[56] References Cited

U.S. PATENT DOCUMENTS

| | | | |
|---|---|---|---|
| 4,182,917 | 1/1980 | Seifert et al. | 568/771 |
| 4,387,252 | 6/1983 | Jupe et al. | 568/771 |
| 4,804,788 | 2/1989 | Konai et al. | 568/771 |
| 4,814,521 | 3/1989 | Tanonaka et al. | 568/771 |

FOREIGN PATENT DOCUMENTS

| | | | |
|---|---|---|---|
| 0046918 | 3/1982 | European Pat. Off. | 568/771 |
| 0397553 | 11/1990 | European Pat. Off. | |
| 1079454 | 11/1954 | France | 568/771 |
| 2071464 | 9/1971 | France . | |
| 2266683 | 10/1975 | France . | |
| 2563446 | 10/1985 | France . | |
| 2667598 | 4/1992 | France . | |
| 3632075 | 3/1988 | Germany | 568/771 |
| 0126628 | 10/1975 | Japan | 568/771 |
| 0046385 | 2/1985 | Japan | 568/771 |

*Primary Examiner*—Werren B. Lone
*Attorney, Agent, or Firm*—Burns, Doane, Swecker & Mathis

[57] ABSTRACT o-Dihydroxylated aromatic compounds, for example pyrocatechol, are selectively prepared by reacting an o-fuchsone with an oxidizing agent, for example hydrogen peroxide, optionally in the presence of a catalytically effective amount of an acid catalyst.

23 Claims, No Drawings

PREPARATION OF O-DIHYDROXYLATED AROMATIC COMPOUNDS VIA OXIDATION OF O-FUCHSONES

CROSS-REFERENCE TO COMPANION APPLICATION

Our copending application Ser. No. 08/179,234, filed Jan. 10, 1994, filed concurrently herewith and assigned to the assignee hereof.

BACKGROUND OF THE INVENTION

1. Field of the Invention

The present invention relates to the preparation of dihydroxylated aromatic compounds, and, more especially, to the preparation of o-dihydroxylated aromatic compounds, in particular pyrocatechol, via the oxidation of o-fuchsones.

2. Description of the Prior Art

A variety of techniques for hydroxylating phenols are known to this art. Compare, for example, FR-A-2,071,464 and FR-A-2,266,683.

The known methods produce a mixture of diphenols with substantially equal amounts of the ortho and para isomers, but with the ortho isomer predominating.

Need continues to exist, however, in order to respond to fluctuating market demand, for an industrial process which can selectively produce one of these isomers.

SUMMARY OF THE INVENTION

Accordingly, a major object of the present invention is the provision of an improved process for the preparation of dihydroxylated aromatic compounds which are selectively dihydroxylated in the ortho position.

Briefly, the present invention features a process for the preparation of o-dihydroxylated aromatic compounds, comprising reacting an oxidizing agent with an o-fuchsone.

DETAILED DESCRIPTION OF BEST MODE AND PREFERRED EMBODIMENTS OF THE INVENTION

More particularly according to the present invention, by the term "o-fuchsone" is intended any chemical compound comprising the following 1-methylene 2-quinone structural unit:

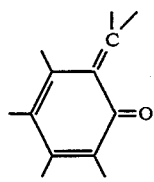

The final product according to the invention is an o-dihydroxylated aromatic compound. By "aromatic compound" is intended the conventional concept of aromaticity as defined in the literature, particularly in Jerry March, *Advanced Organic Chemistry*, 3rd edition, pp. 37 et seq, John Wiley and Sons (1985).

In accordance with the process of the invention, an o-dihydroxylated aromatic compound is obtained by oxidation of an o-fuchsone.

The o-fuchsone may be used in its anhydrous or hydrated state, or as a mixture of the two.

Thus, a non-hydrated o-fuchsone can be represented by the general formula (I):

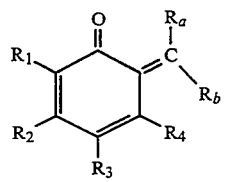

in which $R_a$ and $R_b$, which may be identical or different, are each a hydrocarbon radical having from 3 to 30 carbon atoms, the carbon atoms of each radical $R_a$ and $R_b$ in the α-position with respect to the carbon atom bonded thereto being tertiary carbon atoms, and $R_1$, $R_2$, $R_3$ and $R_4$, which may be identical or different, are each a hydrogen atom or any inert substituent, with the proviso that $R_1$ and $R_2$ and/or $R_2$ and $R_3$ and/or $R_3$ and $R_4$ borne by adjacent carbon atoms may together form, with the carbon atoms from which they depend, a cyclic ring member.

The o-fuchsone can also be employed in its hydrated "carbinol" form, which can be represented by the following general formula (II):

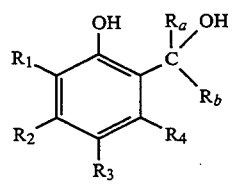

In said formula (II), the various symbols $R_1$, $R_2$, $R_3$, $R_4$, $R_a$ and $R_b$ are as defined above.

A mixture of fuchsones of the formulae (I) and (II) can also be used.

The fuchsones of formulae (I) and (II) may bear one or more substituents $R_1$, $R_2$, $R_3$ or $R_4$. Exemplary such substituents are set forth below. Any substituent may be present on the basic nucleus providing that it does not interfere with the desired final product, i.e., is "inert."

The process of the invention is preferably applicable to compounds having formulae (I) and/or (II) wherein $R_1$, $R_2$, $R_3$ and $R_4$, which may be identical or different, are each a radical $R_0$, namely, a hydrogen atom, a linear or branched alkyl radical having from 1 to 6 carbon atoms, preferably 1 to 4 carbon atoms, such as methyl, ethyl, propyl, isopropyl, butyl, sec-butyl, tert-butyl, a linear or branched alkenyl radical having from 1 to 6 carbon atoms, preferably 2 to 4 carbon atoms, such as vinyl, allyl, a linear or branched alkoxy radical having from 1 to 6 carbon atoms, preferably 1 to 4 carbon atoms, such as methoxy, ethoxy, propoxy, isopropoxy, butoxy, an acyl radical having 2 to 6 carbon atoms, a radical of the formulae:

—$R_5$—OH

—$R_5$—COOR$_6$

—$R_5$—X

—$R_5$—CF$_3$ wherein $R_5$ is a valence bond or a linear or branched, saturated or unsaturated divalent hydrocarbon radical having from 1 to 6 carbon atoms such as, for example, methylene, ethylene, propylene, isopropylene, isopropylidene, $R_6$ is a hydrogen atom or a linear or branched alkyl radical having from 1 to 6 carbon atoms, and X is a halogen atom, preferably a chlorine, bromine or fluorine atom; or wherein at least one of $R_1$, $R_2$, $R_3$ and $R_4$, which may be identical or different, is a radical $R_7$, namely, a saturated or unsaturated carbocyclic radical having from 4 to 7 carbon atoms, preferably a cyclohexyl radical, a radical having the formula:

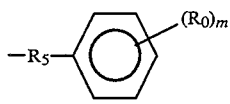

wherein $R_5$ is a valence bond or a linear or branched, saturated or unsaturated divalent hydrocarbon radical having from 1 to 6 carbon atoms, such as, for example, methylene, ethylene, propylene, isopropylene, isopropylidene, $R_0$ is as defined above and m is a whole number ranging from 0 to 4, a radical —$R_5$—A—$R_8$ wherein $R_5$ is as defined above, $R_8$ is a linear or branched alkyl radical having from 1 to 6 carbon atoms or a radical:

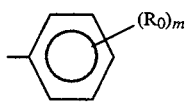

and A is one of the following groups:

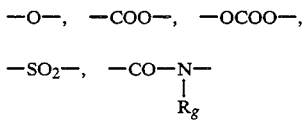

wherein $R_g$ is a hydrogen atom or an alkyl radical having from 1 to 4 carbon atoms, a cyclohexyl or a phenyl radical, with the proviso that $R_1$ and $R_2$ and/or $R_2$ and $R_3$ and/or $R_3$ and $R_4$ borne by adjacent carbon atoms may together form, with the carbon atoms from which they depend, an unsaturated or aromatic carbocycle having from 4 to 7 carbon atoms, preferably 6 carbon atoms.

Exemplary radicals $R_a$ and $R_b$ include branched alkyl radicals having at least 3 carbon atoms and aryl radicals having at least 6 carbon atoms, more particularly tert-butyl, tert-pentyl, tert-hexyl or phenyl radicals, or optionally substituted such radicals.

Fuchsones that are very well suited for carrying out the process of the present invention have the following general formulae (Ia) and/or (IIa):

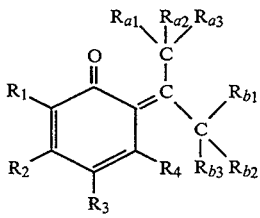

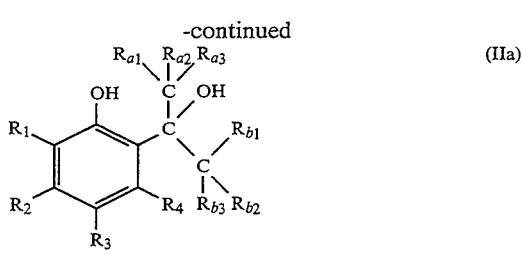

in which $R_{a1}$, $R_{a2}$ and $R_{a3}$ and $R_{b1}$, $R_{b2}$ and $R_{b3}$, which may be identical or different, are each a linear or branched alkyl radical having from 1 to 10 carbon atoms, or a cyclohexyl, phenyl or naphthyl radical, or an optionally substituted such radical, with the proviso that $R_{a1}$, $R_{a2}$ and $R_{a3}$ on the one hand, and $R_{b1}$, $R_{b2}$ and $R_{b3}$ on the other, may together form, with the carbon atom from which they depend, a benzene or naphthalene ring member, or an optionally substituted such carbocycle, and R], $R_2$, $R_3$ and $R_4$, which may be identical or different, are each a hydrogen atom, a linear or branched alkyl radical having from 1 to 4 carbon atoms, a linear or branched alkoxy radical having from 1 to 4 carbon atoms, a hydroxyl group, a halogen atom, a —$CF_3$ group, a cyclohexyl radical, or a phenyl radical, with the proviso that $R_1$ and $R_2$ and/or $R_2$ and $R_3$ and/or $R_3$ and $R_4$ borne by two adjacent carbon atoms may together form, with the carbon atoms from which they depend, a benzene ring.

By "optionally substituted" is intended the presence of one or more inert substituents on the cyclic nuclei. Exemplary such substituents, represented by Y, are set forth below.

More preferably, compounds having formula (Ia) and/or (Iia) are selected from among those wherein one of the radicals $R_1$, $R_2$, $R_3$ and $R_4$ is a hydroxyl group, a methyl radical or a methoxy radical and the other three are hydrogen atoms.

Among the fuchsones of formulae (Ia) and/or (IIa), those preferred have the formulae (Ib) and/or (Ib):

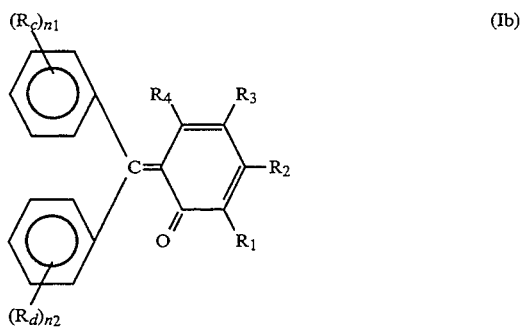

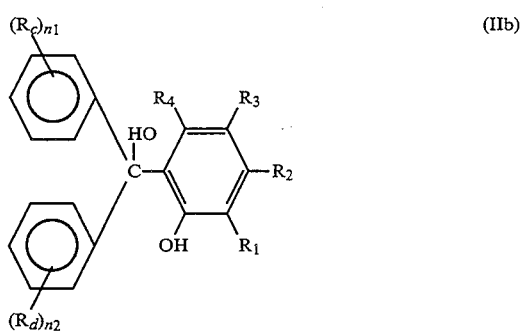

in which $R_1$, $R_2$, $R_3$ and $R_4$, which may be identical or different, are each a hydrogen atom, a linear or branched alkyl radical having from 1 to 4 carbon atoms, a linear or branched alkoxy radical having from 1 to 4 carbon atoms, a hydroxyl group, a halogen atom, a —$CF_3$ group, a cyclohexyl radial, or a phenyl radical, with the proviso that $R_1$ and $R_2$ and/or $R_2$ and $R_3$ and/or $R_3$ and $R_4$ borne by two adjacent carbon atoms may together form, with the carbon atoms from which they depend, a benzene ring, $R_c$ and $R_d$, which may be identical or different, are each a hydrogen atom or an inert substituent, and $n_1$ and $n_2$, which may be identical or different, are each a number equal to 0, 1, 2 or 3.

Substituent Y is selected such that it does not react under the acid conditions employed in the process of the invention.

Exemplary such inert substituents include linear or branched alkyl radicals having from 1 to 4 carbon atoms, a phenyl radical, $R_{10}$—O alkoxy radicals wherein $R_{10}$ is a linear or branched alkyl radical having from 1 to 4 carbon atoms or the phenyl radical, the hydroxyl group, and halogen atoms, preferably chlorine, bromine or fluorine.

Preferred fuchsones according to the present invention are those corresponding to general formulae (Ib) and/or (IIb) wherein $R_c$ and $R_d$, which may be identical or different, are each a hydrogen atom or an inert substituent as defined above, with $R_c$ and $R_d$ preferably being in the 4,4′ position and $n_1$ and $n_2$, which may be identical or different, are each equal to 0 or 1.

Other preferred fuchsones are those corresponding to formulae (Ib) and/or (IIb) wherein $R_c$ and $R_d$, which may be identical or different, are each a hydrogen atom, a methyl, ethyl, tert-butyl, or phenyl radical, a methoxy or ethoxy radical, or a hydroxyl group, with $R_c$ and $R_d$ preferably being in the 3,3′ or 4,4′ position.

Specific examples of fuchsones which are well suited for the process of the invention are, particularly, o-diphenylfuchsone and/or its carbinol:

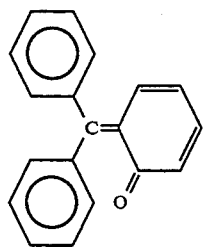

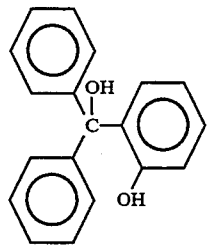

Any fuchsone can be used in the process of the invention, whatever its mode of preparation. Thus, fuchsones can be used prepared by techniques described in the literature, particularly in M. Pisova and M. Soucek, Coll. Czech. Chem. Commun., 47, (12) 3318-27, and J. J. Talley and I. A. Evans, J. Org. Chem., 49, 5267–5269 (1984).

Exemplary oxidizing agents which are well suited for carrying out the process of the invention include hydrogen peroxide, peracids such as peracetic acid, hydroperoxides such as tert-butyl hydroperoxide, cyclohexyl hydroperoxide, and cumyl hydroperoxide.

Among these oxidizing agents, hydrogen peroxide is the preferred.

The hydrogen peroxide used in the process of the invention may be in the form of an aqueous or organic solution.

Aqueous solutions are the preferred, because of their greater commercial availability.

The concentration of the aqueous hydrogen peroxide solution is not critical in itself, but is selected such as to introduce as little water as possible into the reaction medium. In general, an aqueous hydrogen peroxide solution of at least 20 and preferably about 70 weight % of $H_2O_2$ is used.

The amount of hydrogen peroxide used is preferably equal to the stoichiometric amount, i.e., 1 mole of $H_2O_2$ per 1 mole of fuchsone of formulae (I) and/or (II). A slight excess can be used, up to 20% of the stoichiometric amount.

In a preferred embodiment of the invention, the fuchsone and the oxidizing agent are reacted in the presence of an acid catalyst.

An acid catalyst which is a strong acid may participate in the reaction. By "strong acid" is intended an acid having a pka in water of less than $-0.1$, preferably less than $-1.0$.

The Pka is defined as the ionic dissociation constant of the acid/base couple using water as solvent.

Among such acids, it is preferable to use those which are stable to oxidation by hydrogen peroxide.

Particularly representative thereof are the oxyacids which may or may not be halogenated, such as sulfuric acid, pyrosulfuric acid, perchloric acid, halogenosulfonic acids such as fluorosulfonic acid, chlorosulfonic acid or trifluoromethanesulfonic acid, methanesulfonic acid, ethanesulfonic acid, ethanedisulfonic acid, benzenesulfonic acid, benzenedisulfonic acids, toluenesulfonic acids, naphthalenesulfonic acids and napthalenedisulfonic acids.

Among these acids, perchloric acid, trifluoromethanesulfonic acid, paratoluenesulfonic acid, chlorosulfonic acid, fluorosulfonic acid and methanesulfonic acid are the preferred.

Particularly preferred acids are perchloric acid, trifluoromethanesulfonic acid and methanesulfonic acid.

The amount of acid used, expressed by the ratio of number of proton equivalents to the number of moles of hydrogen peroxide, advantageously ranges from about $1 \cdot 10^{-4}$ to 1.0.

In a preferred embodiment of the invention, a $H^+/H_2O_2$ ratio of $1 \cdot 10^{-3}$ to 0.1 is employed.

The reaction is advantageously carried out in the liquid phase. Thus, the fuchsone is initially dissolved in an organic solvent which may be the dihydroxylated aromatic compound to be obtained and/or any protic or aprotic, polar or apolar organic solvent, provided that it is appropriate for the present invention.

Several requirements determine the selection of the solvent.

The organic solvent must be stable under the conditions of the subject reaction. Solvents which are not stable in the reaction medium and which degrade by oxidation are excluded from the present invention.

The organic solvent must, preferably, dissolve both the oxidizing agent and the fuchsone which is present.

In addition, it is desirable that the organic solvent not be too basic, i.e., its basicity should be such that it has a donor number of less than 25. The donor number provides an estimate of the basicity of a solvent. This donor number, abbreviated to DN, provides an indication of the nucleophilic character of the solvent and its tendency to donate its electron pair.

The definition of donor number is given in Christian Reinhardt, *Solvents and Solvent Effects in Organic Chemistry*, VCH, p. 19 (1988), namely, the negative ($-\Delta H$) of the enthalpy (Kcal/mol) of interaction between the solvent and antimony pentachloride in dichloroethane solution.

The following organic solvents are suitable for use in the process of the present invention:

(i) phenol, (ii) aliphatic or aromatic nitriles, such as acetonitrile, propionitrile, butanenitrile, isobutanenitrile, benzonitrile, benzyl cyanide, (iii) aliphatic, cycloaliphatic or aromatic ether/oxides and, more particularly, diethyl oxide, dipropyl oxide, diisopropyl oxide, dibutyl oxide, methyltertiobutylether, dipentyl oxide, diisopentyl oxide, ethyleneglycol dimethylether (or 1,2-dimethoxyethane), diethyleneglycol dimethylether (or 1,5-dimethoxy-3-oxapentane), dioxane, tetrahydrofuran, (iv) chlorinated aliphatic hydrocarbons, for example dichloromethane, tetrachloromethane, dichloroethane, (v) alcohols such as methanol, ethanol, isopropanol, teriobutanol.

A mixture of solvents may also be used, in particular a mixture of the phenolic compound to be obtained and an organic solvent.

The amount of organic solvent used is a function of the solubility of the fuchsone in said organic solvent.

The concentration of the fuchsone in the organic solvent may vary widely. It advantageously ranges from 0.1 to 2 moles/liter.

In accordance with the process of the invention, the fuchsone is reacted with the oxidizing agent, if necessary in the presence of an acid catalyst, at a temperature which advantageously ranges from 20° C. to 150° C.

In a preferred embodiment of the invention, the temperature ranges from 30° C. to 80° C.

The reaction is preferably carried out at atmospheric pressure.

The reaction can readily be carried out in either continuous or discontinuous fashion.

The different reactants can be introduced in any order, provided that the oxidizing agent is introduced last. Preferably, the reactants are introduced in the following order: the fuchsone having formula (I) and/or (II), the reaction solvent and the acid catalyst.

The reaction medium is heated to the desired temperature and the oxidizing agent, preferably hydrogen peroxide, is then gradually introduced.

At the end of the reaction, the hydroxylation products are separated using standard techniques, in particular distillation.

The method of the invention selectively produces o-dihydroxylated aromatic compounds.

In order to further illustrate the present invention and the advantages thereof, the following specific examples are given, it being understood that same are intended only as illustrative and in nowise limitative.

In said examples to follow, the abbreviations have the following definition:

$$RR_{PC/FUCHSONE} = \frac{\text{number of moles of pyrocatechol formed}}{\text{number of moles of fuchsone introduced}} \ \%$$

EXAMPLE 1

The o-diphenylfuchsone used in this example was prepared in known fashion in accordance with the procedure of M. Pisova and M. Soucek, *Coll. Czech. Chem. Commun.*, 47, (12), 3318–27. It had the formula:

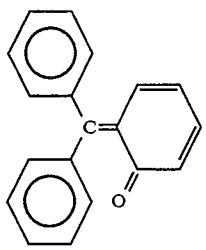

Pyrocatechol was then prepared according to the present invention.

The following reagents were placed in a 25 ml flask provided with a magnetic stirrer:

(i) 0.774 g (3 mmol) o-diphenylfuchsone, (ii) 8.3 ml acetonitrile, (iii) 0.113 ml (3 mmol) hydrogen peroxide, as a 70% by weight aqueous solution thereof, and (iv) 2 drops of 70% by weight perchloric acid.

The temperature increased slightly, then the mixture was heated to 30° C. for 1 hour.

The reaction products were immediately analyzed using high performance liquid chromatography.

The following were determined in the reaction medium:

(a) 2.40 mmol pyrocatechol RR=80%

(b) 2.40 mmol benzophenone RR=80%.

EXAMPLE 2

In this example 2-hydroxy triphenylcarbinol was used that was prepared in accordance with the procedure of J. J. Talley and I. A. Evans, *J. Org. Chem.*, 49, 5267–5269 (1984).

22.5 g (0.13 mol) of orthobromophenol in solution in 100 ml anhydrous ethyl ether were introduced into a mixture of 164 ml (0.26 mol) of n-butyllithium in hexane solution and 200 ml of ether in a one liter glass reactor provided with a central stirrer, a 250 ml tapped funnel, a condenser and a temperature gauge, all in an argon atmosphere. The mixture temperature was maintained at about 0° C. during the period of addition (45 min), then it was permitted to increase naturally to room temperature. The total reaction time was 2 hours, 45 min.

Condensation of the benzophenone on the organolithium was carried out by addition, over 30 min, of an ether solution of 23.7 g (0.13 mol) of benzophenone at a temperature of about −70° C., then permitting the temperature to increase to room temperature. The total duration was 1 hour.

The reaction medium was then hydrolyzed by slowly adding an aqueous solution of ammonium chloride, controlling the exothermicity, at a temperature of about 0° C. The ether phase was separated from the aqueous layer, washed with water, dried over magnesium sulfate and vacuum evaporated.

The residue obtained was recrystallized hot from 350 ml of cyclohexane with 0.2 g of carbon black 3S.

After drying, 17.9 g of a white solid having the following formula were obtained:

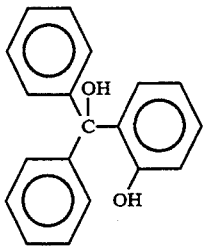

This had a melting point of 152° C. Its 1H-NMR spectrum was as expected.

Pyrocatechol was then prepared from the 2-hydroxy triphenylcarbinol thus obtained.

0.828 g (3 mmol) of 2-hydroxy triphenylcarbinol, 8.3 ml of acetonitrile, 0.113 ml of 70% (3 mmol) hydrogen peroxide and 2 drops of 70% perchloric acid were introduced into a 25 ml flask provided with a magnetic stirrer.

The temperature increased slightly, then it was heated to 70° C. for 1 hour.

The reaction products were immediately analyzed using gaseous phase chromatography and high performance liquid chromatography.

In the reaction medium, the following were determined:

(a) 2.44 mmol of pyrocatechol RR=81.3%

(b) 2.40 mmol of benzophenone RR=80%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an o-dihydroxylated aromatic compound, comprising reacting an oxidizing agent with an o-fuchsone, said o-fuchsone being in an anhydrous or hydrated state, or a mixture thereof.

2. The process as defined by claim 1, said o-fuchsone comprising at least one compound having the formulae (I) or (II):

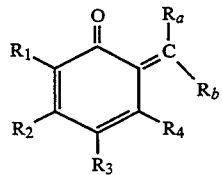

(I)

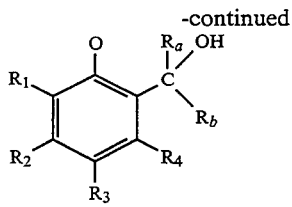

(II)

in which $R_a$ and $R_b$, which may be identical or different, are each a hydrocarbon radical having from 3 to 30 carbon atoms, the carbon atoms of each radical $R_a$ and $R_b$ in the α-position with respect to the carbon atom bonded thereto being tertiary carbon atoms, and $R_1$, $R_2$, $R_3$ and $R_4$, which may be identical or different, are each a hydrogen atom or inert substituent, with the proviso that one or more of (i) $R_1$ and $R_2$, (ii) $R_2$ and $R_3$, and (iii) $R_3$ and $R_4$ may together form, with the carbon atoms from which they depend, a ring member.

3. The process as defined by claim 2, wherein $R_1$, $R_2$, $R_3$ and $R_4$, which may be identical or different, are each a radical $R_0$ selected from among a hydrogen atom, a linear or branched alkyl radical having from 1 to 6 carbon atoms, a linear or branched alkenyl radical having from 2 to 6 carbon atoms, a linear or branched alkoxy radical having from 1 to 6 carbon atoms, an acyl radical having 2 to 6 carbon atoms, a radical having the formulae:

—$R_5$—OH

—$R_5$—COOR$_6$

—$R_5$—X

—$R_5$—CF$_3$ wherein $R_5$ is a valence bond or a linear or branched, saturated or unsaturated divalent hydrocarbon radical having from 1 to 6 carbon atoms, $R_6$ is a hydrogen atom or a linear or branched alkyl radical having from 1 to 6 carbon atoms, and X is a halogen atom; or at least one of $R_1$, $R_2$, $R_3$ and $R_4$, which may be identical or different, is a radical $R_7$ selected from among a saturated or unsaturated carbocyclic radical having from 4 to 7 carbon atoms, a radical having the formula:

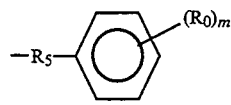

wherein $R_5$ is a valence bond or a linear or branched, saturated or unsaturated divalent hydrocarbon radical having from 1 to 6 carbon atoms, $R_0$ is as defined above and m is a whole number ranging from 0 to 4, a radical —$R_5$—A—$R_8$ wherein $R_5$ is as defined above, $R_8$ is a linear or branched alkyl radical having from 1 to 6 carbon atoms, or a radical:

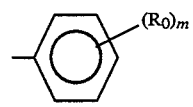

and A is one of the following groups:
—O—, —COO—, —OCOO—, —SO$_2$—, $$-CO-N-,$$
$$\phantom{-CO-N}|$$
$$\phantom{-CO-N}R_g$$

wherein $R_g$ is a hydrogen atom or an alkyl radical having from 1 to 4 carbon atoms, a cyclohexyl or a phenyl radical, with the proviso that one or more of (i) $R_1$ and $R_2$, (ii) $R_2$ and $R_3$, and (iii) $R_3$ and $R_4$ may together form, with the carbon atoms from which they depend, an unsaturated or aromatic carbocycle having from 4 to 7 carbon atoms.

4. The process as defined by claim 2, wherein $R_a$ and $R_b$ are each a branched alkyl radical having at least 3 carbon atoms, or an aryl radical having at least 6 carbon atoms, or a substituted such radical.

5. The process as defined by claim 1, said o-fuchsone comprising at least one compound having the general formulae (Ia) or (IIa):

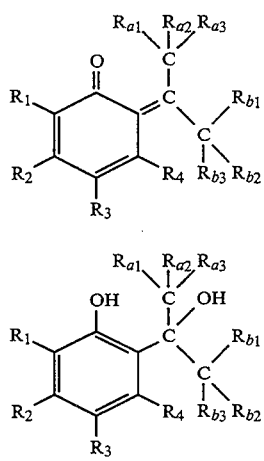

in which $R_{a1}$, $R_{a2}$ and $R_{a3}$ and $R_{b1}$, $R_{b2}$ and $R_{b3}$, which may be identical or different, are each a linear or branched alkyl radical having from 1 to 10 carbon atoms, or a cyclohexyl, phenyl or naphthyl radical, or a substituted such radical, with the proviso that $R_{a1}$, $R_{a2}$ and $R_{a3}$ and/or $R_{b1}$, $R_{b2}$ and $R_{b3}$ may together form, with the carbon atom from which they depend, a benzene or naphthalene ring, or a substituted such ring member, and $R_1$, $R_2$, $R_3$ and $R_4$, which may be identical or different, are each a hydrogen atom, a linear or branched alkyl radical having from 1 to 4 carbon atoms, a linear or branched alkoxy radical having from 1 to 4 carbon atoms, a hydroxyl group, a halogen atom, a —$CF_3$ group, a cyclohexyl radical, or a phenyl radical, with the proviso that one or more of (i) $R_1$ and $R_2$, (ii) $R_2$ and $R_3$, and (iii) $R_3$ and $R_4$ may together form, with the carbon atoms from which they depend, a benzene ring.

6. The process as defined by claim 5, wherein one of the radicals $R_1$, $R_2$, $R_3$ and $R_4$ is a hydroxyl group, a methyl radical or a methoxy radical and the other three are hydrogen atoms.

7. The process as defined by claim 1, said o-fuchsone comprising at least one compound having the formulae (Ib) or (IIb):

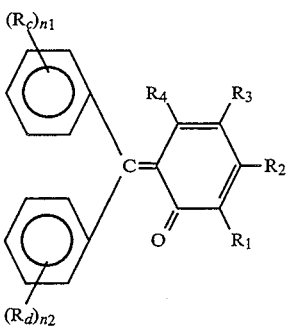

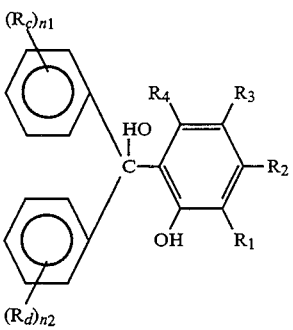

in which $R_1$, $R_2$, $R_3$ and $R_4$, which may be identical or different, are each a hydrogen atom, a linear or branched alkyl radical having from 1 to 4 carbon atoms, a linear or branched alkoxy radical having from 1 to 4 carbon atoms, a hydroxyl group, a halogen atom, a —$CF_3$ group, a cyclohexyl radial, or a phenyl radical, with the proviso that one or more of (i) $R_1$ and $R_2$, (ii) $R_2$ and $R_3$, and (iii) $R_3$ and $R_4$ may together form, with the carbon atoms from which they depend, a benzene ring; $R_c$ and $R_d$, which may be identical or different, are each a hydrogen atom or an inert substituent; and $n_1$ and $n_2$, which may be identical or different, are each 0, 1, 2 or 3.

8. The process as defined by claim 7, wherein $R_c$ and $R_d$, which may be identical or different, are each a linear or branched alkyl radical having from 1 to 4 carbon atoms, a phenyl radical, $R_{10}$—O alkoxy radical wherein $R_{10}$ is a linear or branched alkyl radical having from 1 to 4 carbon atoms or a phenyl radical, a hydroxyl group, or a halogen atom.

9. The process as defined by claim 7, wherein $R_c$ and $R_d$, which may be identical or different, are in the 4,4'-positions, are each a hydrogen atom, linear or branched alkyl radical having from 1 to 4 carbon atoms, a phenyl radical, an $R_{10}$—O alkoxy radical wherein $R_{10}$ is a linear or branched alkyl radical having from 1 to 4 carbon atoms or a phenyl radical, a hydroxyl group, or a halogen atom, and $n_1$ and $n_2$, which may be identical or different, are each 0 or 1.

10. The process as defined by claim 8, wherein $R_c$ and $R_d$, which may be identical or different, are each a hydrogen atom, a methyl, ethyl, tert-butyl, or phenyl radical, a methoxy or ethoxy radical, or a hydroxyl group, and $R_c$ and $R_d$ are in the 3,3'- or 4,4'-position.

11. The process as defined by claim 1, said o-fuchsone comprising o-diphenylfuchsone in anhydrous or hydrated state, or mixture thereof.

12. The process as defined by claim 1, said oxidizing agent comprising hydrogen peroxide, a peracid, or a hydroperoxide.

13. The process as defined by claim 12, said oxidizing agent comprising an aqueous solution of hydrogen peroxide.

14. The process as defined by claim 13, carried out using a stoichiometric amount of hydrogen peroxide.

15. The process as defined by claim 1, carried out in the presence of a catalytically effective amount of a strong acid catalyst.

16. The process as defined by claim 15, said strong acid catalyst comprising sulfuric acid, pyrosulfuric acid, perchloric acid, fluorosulfonic acid, chlorosulfonic acid, trifluoromethanesulfonic acid, methanesulfonic acid, ethanesulfonic acid, ethanedisulfonic acid, benzenesulfonic acid, a benzenedisulfonic acid, a toluenesulfonic acid, a naphthalenesulfonic acid or a naphthalenedisulfonic acid.

17. The process as defined by claim 16, said strong acid catalyst comprising perchloric acid, trifluoromethanesulfonic acid or methanesulfonic acid.

18. The process as defined by claim 15, wherein the amount of acid, expressed by the ratio of number of proton equivalents to the number of moles of oxidizing agent, ranges from about $1 \cdot 10^{-4}$ to 1.0.

19. The process as defined by claim 1, carried out in the presence of an organic solvent.

20. The process as defined by claim 19, said organic solvent comprising phenol, an aliphatic or aromatic nitrile, an aliphatic, cycloaliphatic or aromatic ether/oxide, a chlorinated aliphatic hydrocarbon or an alcohol.

21. The process as defined by claim 1, carried out at a reaction temperature ranging from 20° C. to 150° C.

22. The process as defined by any one of claims 2–10, said oxidizing agent comprising hydrogen peroxide, a peracid, or a hydroperoxide and wherein the reaction is carried out in the presence of a catalytically effective amount of a strong acid catalyst.

23. The process as defined by claim 22, carried out in the presence of an organic solvent.

* * * * *